US00PP19311P2

(12) United States Plant Patent

Walters et al.

(10) Patent No.: US PP19,311 P2

(45) Date of Patent: Oct. 7, 2008

(54) *COREOPSIS* PLANT NAMED 'SUNBEAM'

(50) Latin Name: *Coreopsis verticillata*
Varietal Denomination: Sunbeam

(75) Inventors: Ronald L. Walters, deceased, late of Hudsonville, MI (US); by Sharon Walters, legal representative, Hudsonville, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 11/894,824

(22) Filed: Aug. 22, 2007

(51) Int. Cl.
*A01H 5/00* (2006.01)

(52) U.S. Cl. ..... Plt./417

(58) Field of Classification Search ..... Plt./417
See application file for complete search history.

(56) References Cited

U.S. PATENT DOCUMENTS

PP16,096 P2 * 11/2005 Croon ..... Plt./417

* cited by examiner

*Primary Examiner*—Wendy C. Haas

(57) ABSTRACT

The new and distinct *Coreopsis verticillata* plant named 'Sunbeam' with narrow foliage, yellow flowers having rounded apices and long flowering for cut flower, or landscaping in mass or as a specimen plant.

2 Drawing Sheets

Botanical designation: *Coreopsis verticillata.*
Cultivar denomination: 'Sunbeam'.

BACKGROUND OF THE PLANT

The present invention relates to the new and distinct Threadleaf Coreopsis herein also referred to as *Coreopsis verticillata* 'Sunbeam', by the cultivar name, 'Sunbeam', or as the Plant. 'Sunbeam' was discovered by Ronald L. Walters in the summer of 2002 as an uninduced whole plant mutation of Coreopsis 'Moonbeam' (not patented) in the fields of a wholesale perennial grower in Zeeland, Mich., USA. It was then isolated and compared in subsequent years to other *coreopsis* and found to be different from all cultivars known to the discoverer.

Asexual propagation at the same nursery in Zeeland, Mich. USA by cuttings has shown 'Sunbeam' to be stable and reproduce true to type in successive generations.

SUMMARY OF THE PLANT

The Plant has not been observed in all possible environmental conditions. The phenotype may vary slightly with changes in environments such as light intensity, fertility, water availability, etc. without, however any variation in genotype.

'Sunbeam' is distinct from all known cultivars in the following traits:

1. Narrow foliage with moderate height.
2. Petite flowers held above the foliage with deep yellow ray petals.
3. Long flowering period.

NEAREST COMPARISON

Plants of 'Sunbeam' are shorter in habit than 'Golden Showers' (not patented) and taller than 'Zagreb' (not patented). Flowers of 'Sunbeam' are smaller, with entire margins on ray petals and the flowers are above the foliage compared to 'Créme Brutée' U.S. Plant Pat. No. 16,096 which hare larger flowers held at the foliage level and incised ray petal apices. The ray petal color of 'Sunbeam' is slightly darker yellow than 'Crméme Brulée'.

BRIEF DESCRIPTION OF THE DRAWINGS

The color photographs illustrate the overall characteristics of the Plant. The colors are as true as reasonably possible given the technology available. The color values may vary slightly depending on light intensity and quality.

DETAILED BOTANICAL DESCRIPTION

Figure 1:
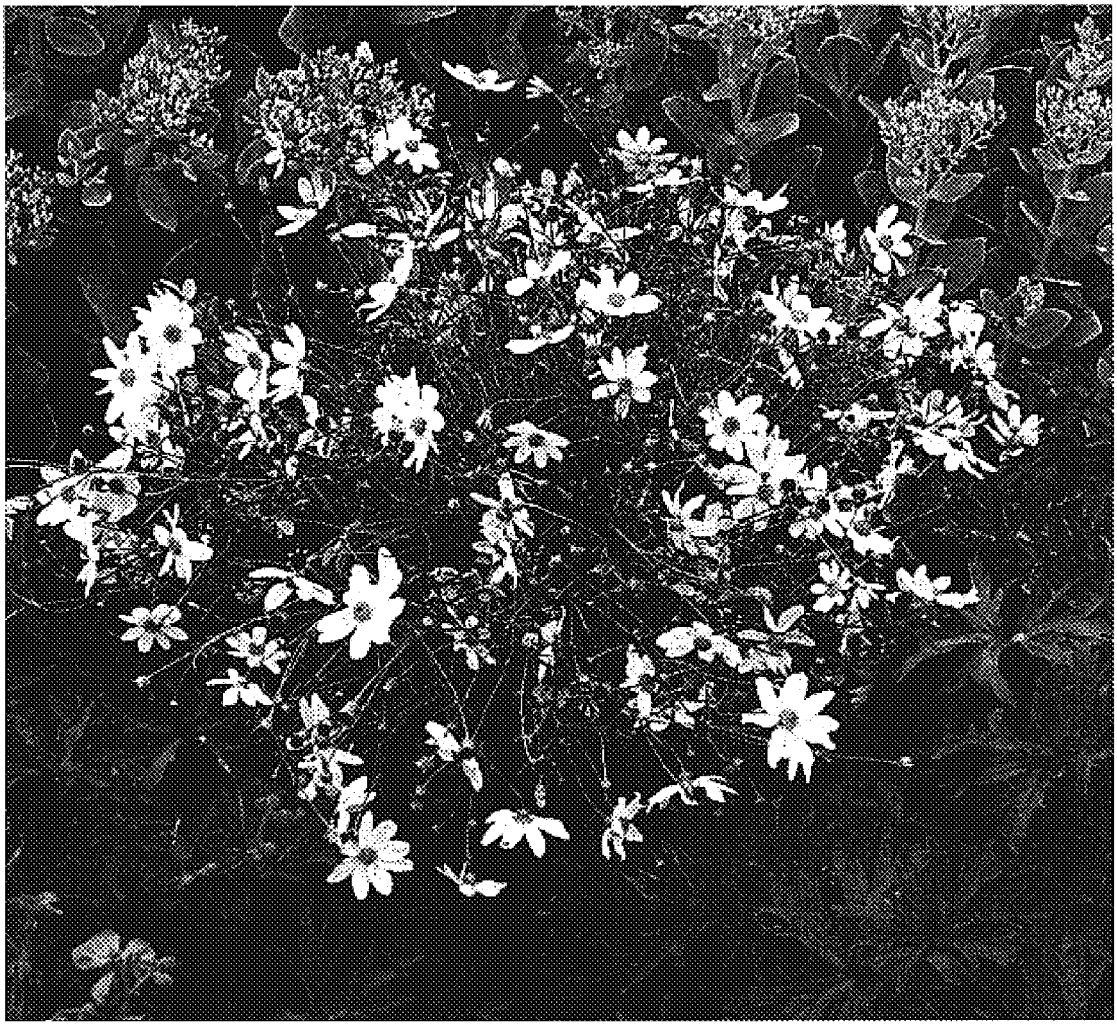
FIG. 1 shows the habit of the Plant in flower in mid summer.
Figure 2:
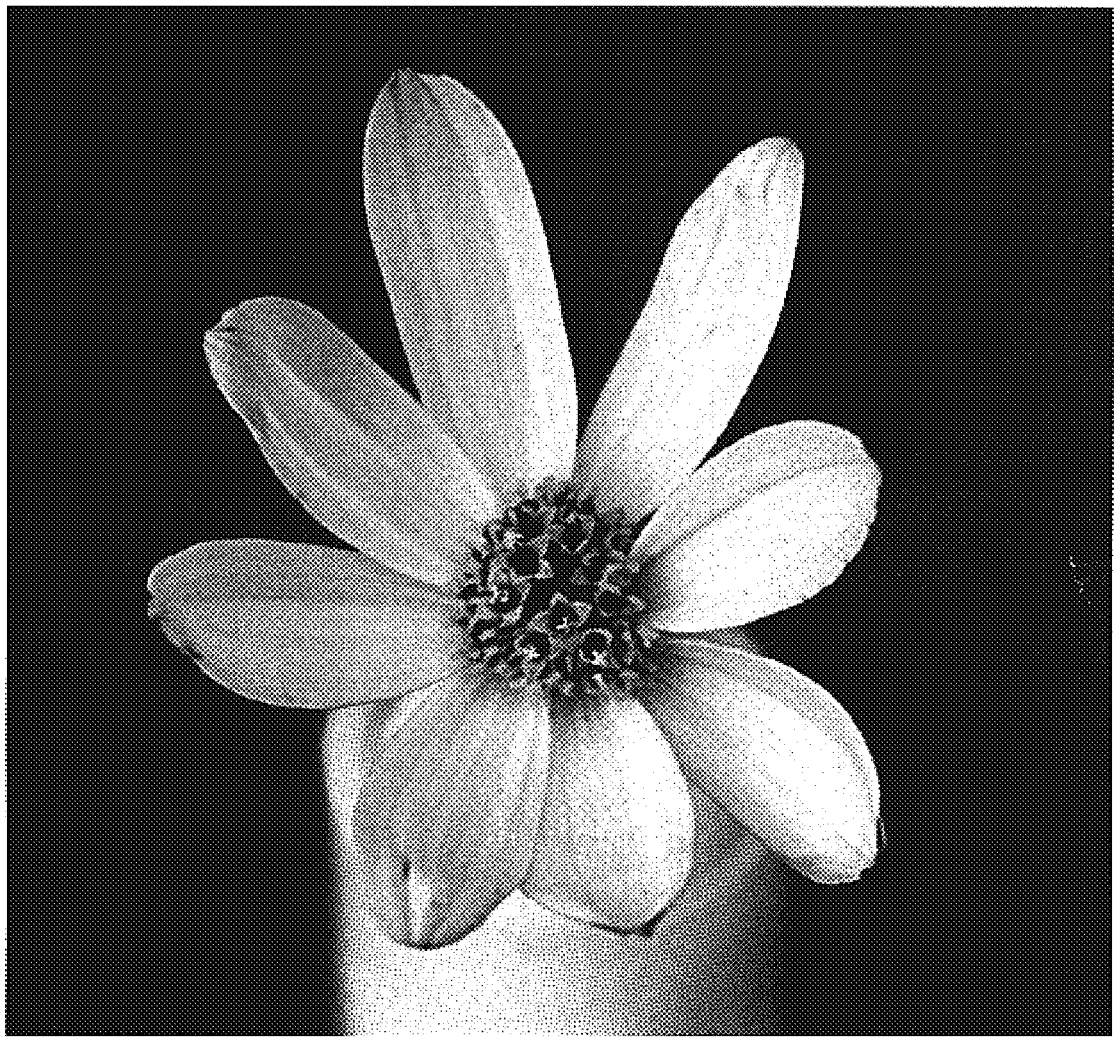
FIG. 2 shows a close-up of the flower.

The following description is based on a two-year old plant growing in a full-sun trial garden in Zeeland, Mich., USA. For the growing season up to the time of description the daytime temperatures range between 12–30° C., and night temperatures range between 6–19° C. Except for ordinary dictionary color usage, color references are according to The Royal Horticultural Society Colour Chart, 2001 edition.

Parentage: Non-induced mutation of 'Moonbeam' (not patented).

Asexual propagation: Cuttings, about 10 to 14 days to initiate roots; time to finish as #1 field grown, 9 months;

Plant habit: Freely basally and axillarily branched, rounded, herbaceous perennial mound; 50 to 60 cm wide, 50 to 55 cm tall;

Leaves: Opposite, entire, glabrous, acute apex; base attenuate; apetiolus; up to 3 cm long and 2 mm wide: RHS 135A on top and RHS 139A on lower surfaces;

Veins: Not obvious;

Flower: Composite consisting of ray and disc florets; on terminal branches; 3.5 cm diameter, 1.0 cm tall from outer set of involucral bracts to top of disc florets;

Sepals:

Phyllary: In two distinct whorls, outer whorl consisting of about 10, about 2 mm long, acute apex, narrowly deltoid, truncate base, glabrous, between RHS 144A and RHS 144B; inner whorl tight against ray petals, usually 8 in number, 5 mm long and 2 mm wide, acute apex and truncate base, closer to RHS 9B at apex and RHS 144A at base;

Fragrance: Not detected;

Flowering period: Early summer through early autumn; producing over 40 flowers per stem and over 200 flowers per plant;

Flower longevity: 5 to 8 days;

Flower buds: One to two days before showing ray petal color spherical with slightly flattened top, 4.0 mm wide and 4.0 mm diameter; near RHS 144B;

Peduncle; Glaucous, thin wiry, strong, many branched; 5.0 mm wide at base; RHS 147B;

Pedicel: Glaucous, thin, wiry, strong; less than 1 mm in diameter, 4 to 5 cm long, RHS 147B.

Ray florets: Usually 8 per flower; oblong elongate, apex rounded, margin entire; base narrowly cuneate; opening to form 180° angle; parallel veined; glabrous on both surfaces, 1.7 to 2.0 cm long and 6 to 7 mm wide; RHS 9A on both surfaces; corolla tube about 2.0 mm long; containing only gynoecium with style 2 to 3 mm long and split stigma; both style and stigma color closest to RHS 9A;

Disc florets: 30 to 60 per head; consisting of tepals, staminal tube and pistil;

Tepals: Five; 5 mm long and 1 mm wide, fused in the basal 4 mm, acute apex, color between RHS 151B and RHS 151A;

Staminal tube: Made up of five fused stamens, 2 to 3 mm long, RHS 174A;

Anther: About 1 mm long, closest to RHS 187A;

Pollen: Fine, round, closest to RHS 21C;

Style: About 4.5 mm long; RHS 160B;

Stigma: Split in half and curling back as it matures; RHS 160C;

Seed: Rarely observed.

'Sunbeam' is tolerant of winter temperatures as low as −20° C. and summer temperatures of 40° C. Tolerant of dry summer conditions but does best with ample moisture; Not known to be tolerant of diseases and pest that are common to other *Coreopsis* cultivars.

I claim:

1. The new and distinct cultivar of *Coreopsis* plant named 'Sunbeam' as described and illustrated, with yellow un-fringed petals, fine thread-like foliage and long flowering period.

* * * * *